United States Patent [19]

Vander Meer et al.

[11] Patent Number: 5,587,401
[45] Date of Patent: Dec. 24, 1996

[54] REPELLENTS FOR ANTS

[75] Inventors: Robert K. Vander Meer; William A. Banks; Clifford S. Lofgren, all of Gainesville, Fla.

[73] Assignee: The United States of America as represented by the Secretary of Agriculture, Washington, D.C.

[21] Appl. No.: 471,354

[22] Filed: Jun. 6, 1995

Related U.S. Application Data

[62] Division of Ser. No. 286,111, Aug. 4, 1994, which is a continuation of Ser. No. 925,685, Aug. 7, 1992, abandoned.

[51] Int. Cl.$^6$ ............................ A01N 35/02; A01N 35/04
[52] U.S. Cl. ............................ 514/675; 514/678; 514/919
[58] Field of Search ................................. 514/675, 678, 514/919; 424/DIG. 10

[56] References Cited

U.S. PATENT DOCUMENTS

| | | | |
|---|---|---|---|
| 4,565,695 | 1/1986 | Guss et al. | 424/84 |
| 4,921,696 | 5/1990 | Vander Meer et al. | 424/84 |
| 5,112,638 | 5/1992 | Cagley et al. | 424/640 |

OTHER PUBLICATIONS

Regnier et al, "The Alarm–Defence System of the Ant *Lasius Alienus*", Journal of Insect Physiology, vol. 15, pp. 893–898, 1969.

Crewe et al, "Identification of the Alarm Pheromones of the Ant *Myrmica Brevinodis*", Journal of Insect Physiology, vol. 16, pp. 141–146, 1970.

Crewe et al, "Alarm Pheromones of the Attini: Their Phylogenic Significance", Journal of Insect Physiology, vol. 18, pp. 31–42, 1972.

Cardarelli, "New Concepts in the Application of Controlled Release Systems to Agriculture", American Chemical Society Symposium Series, vol. 33, pp. 208–214, 1976.

Harris et al, "Polymers Containing Pendant Herbicide Substituents: Hydrolysis Studies II", American Chemical Society Symposium Series, vol. 53, pp. 102–111, 1977.

McCormick et al, "Synthesis, Characterization, and Release Mechanisms of Polymers Containing Pendant Herbicides", American Chemical Society Symposium Series, vol. 53, pp. 112–125, 1977.

Longhurst et al, "Chemical Crypsis in Predatory Ants", Experientia, vol. 35, pp. 870–872, 1978.

Cammaerts et al, "Comparative Study of the Pheromones Emitted by Workers of the Ants *Myrmica Rubra* and *Myrmica Scabrinodis*", Journal of Insect Physiology, vol. 24, pp. 207–214, 1978.

Morgan et al, "The Mandibular Gland Secretiion of the Ant, *Myrmica Scabrinodis*", Physiol. Entomology, vol. 3(2), pp. 107–114, 1978.

Pasteels et al, "Differences Sexuelles dans la Production de Phermones chez *Tetramorium Caespitum* (Formicidae)", C. R. UIEIS sct. francaise, English Language Summery, p. 79, 1979.

Longhurst et al, "A Comparative Analysis of Mandibular Gland Secretions in the Ant Tribe *Tetramoriini*", Insect Biochemistry, vol. 10, pp. 107–112, 1980.

Longhurst et al, "A Multicomponent Mandibular Gland Secretion in the Ponerine Ant *Bothroponera Soror* (Emery)", Journal of Insect Physiology, vol. 26, pp. 551–555, 1980.

Olubajo et al, "4–Heptanone in the Mandibular Gland Secretion of the Nearctic Ant, *Zacryptocerus varians* (Hymenoptera: Formicidae)", Ann. Entomol. Soc. Am., vol. 73(1), pp. 93–94, 1980.

Myers et al, "Polymers Containing Pendent Insecticides", Proc. Int. Symp. *Controlled Release Pestic. Pharm.*, PLenum, NY, pp. 171–190, 1981.

Honda, "Defensive potential of components of the larval osmeterial secretion of papilonid butterflies against ants", Physiological Entomology, vol. 8(2), pp. 173–180, 1983.

Cammaerts et al, "The Volatile Components of the Mandibular Gland Secretion of Workers of the Ants *Myrmica Lobicornis* and *Myrmica Sulcinodis*", Journal of Insect Physiology, vol. 29(8), pp. 659–664, 1983.

Cammaerts et al, "The Pheromonal Activity of chiral 3–Octanol for *Myrmica* Ants", Physiological Entomology, vol. 10, pp. 33–36, 1985.

Vander Meer et al, "Isolation of the Trail Recruitment Pheromone of *Solenopsis invicta*", Journal of Chemical Ecology, vol. 14(3), pp. 825–838, 1988.

*Primary Examiner*—John Pak
*Attorney, Agent, or Firm*—M. Howard Silverstein; John Fado; Gail E. Poulos

[57] ABSTRACT

A method has been discovered for repelling ants by treating objects or areas with effective amounts of compositions that include (a) one or more $C_6$ to $C_8$ carboxylic acids; (b) one or more $C_6$ to $C_{14}$ alcohols; (c) one or more esters which are reaction products of (a) and (b) or an ester which is a reaction product of the repellents and other carboxylic acids or alcohols; (d) one or more $C_6$ to $C_{11}$ carboxylic acid esters; (e) one or more $C_6$ to $C_{14}$ ketones; or (f) mixtures thereof.

1 Claim, 8 Drawing Sheets

REPELLENTS FOR ANTS

This is a division of application Ser. No. 08/286,111 filed on Aug. 4, 1994, which is a continuation of application Ser. No. 07/925,685 filed on Aug. 7, 1992, which is now abandoned.

FIELD OF INVENTION

The present invention relates to repellent compositions for ants, particularly fire ants. The composition comprises an effective amount of a repellent selected from: (i) one or more $C_6$ to C14 alcohols; (ii) one or more $C_6$ to $C_8$ carboxylic acids; (iii) one or more $C_6$ to $C_{11}$ carboxylic acid esters; (v) one or more $C_6$ to C14 ketones; and (v) mixtures thereof.

BACKGROUND OF THE INVENTION

Various species of ants pose significant problems for man from both an economic and a health care point of view. For example, leaf-cutting ant species are a problem in Central and South America, where they can defoliate a citrus tree overnight. Consequently, a non-toxic repellent that would prevent leaf-cutting ants from getting into the trees would be of significant value. Also, in the southern United States, fire ants, Solenopsis invicta, are a substantial pest. For example, foraging fire ants are known to destroy young citrus trees, growing crops, and germinating seeds. This has an economic impact on agriculture in infested areas. Telephone companies spend substantial amounts of money each year on treating their electrical equipment to prevent fire ant invasion because fire ants are attracted to electrical fields and can short out electrical equipment. Further, farm equipment can be damaged by large fire ant mounds. Fire ants also present a problem to wildlife, such as with ground nesting birds and animals. Furthermore, Fire ants are known to excavate the soil from under roadways causing damage.

Fire ants also pose a health care problem to the millions of people stung each year—a significant number of which require medical care. Further, fire ant stings are also blamed for human deaths each year. Consequently, there is much interest in controlling these troublesome insects.

This interest has resulted in much research and resources being expended through the years to develop reagents and methods for controlling fire ants. While many useful insecticide formulations have resulted from this research, the problems associated with ants still exist. This is primarily because the relief gained by insecticide use is only temporary owing to the high reproductive capabilities, the efficient foraging behavior, and the ecological adaptability, of ants. While effective for controlling ants in relatively small defined areas, the use of insecticides, because of their toxicity, can create other problems. For example, some insecticides, which are effective for controlling ants, are banned from use because they pose a significant threat to the environment, including birds and animals. Furthermore, there is pressure from environmental groups to stop, or at least substantially reduce, the application of insecticides in general, and to develop non-toxic reagents for controlling insects. One type of reagent which would be of great interest would be a non-toxic reagent which could repel, or keep ants from invading a particular area or object.

Such a reagent would be of great value in preventing leaf-cutting ants from attacking citrus and other agriculturally important trees. It would also be of great value for preventing fire ants from attacking various biological control agents, such as parasitic wasps, which are used to control a host of crop pests, including those which are harmful to cotton. The parasitic wasps are distributed as pupae in small capsules which are dispersed in the area to be controlled. Adult wasps emerge from the capsule within a matter of days. If the capsules are distributed in an area infested with fire ants, the capsules are quickly found by foraging ants which penetrate the capsule and eat the wasp in its pupal stage—thus greatly decreasing the effectiveness of the use of such biological control agents.

Therefore, there is still a substantial need in the art for reagents, particularly non-toxic reagents, which can be used to prevent ants from invading a particular area or object.

SUMMARY OF THE INVENTION

In accordance with the present invention there is provided a repellent composition for ants, which composition is comprised of:

(i) an effective amount of one or more repellents selected from the group consisting of:
  (a) one or more $C_6$ to $C_8$ carboxylic acids;
  (b) one or more $C_6$ to C14 alcohols represented by the formula:

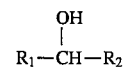

where $R_1$ is H or a $C_1$ to $C_5$ alkyl group, optionally containing olefinic, acetylenic, or aryl moieties; and $R_2$ is a $C_2$ to C13 alkyl group, optionally containing olefinic, acetylenic, or aryl moieties;

(c) one or more $C_6$ to $C_{14}$ ketones represented by the formula:

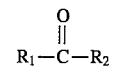

where $R_1$ is a $C_1$ to $C_5$ alkyl group optionally containing olefinic, acetylenic, or aryl moieties; and $R_2$ is a $C_2$ to $C_{13}$ alkyl group optionally containing olefinic, acetylenic, or aryl moieties;

(d) one or more $C_6$ to $C_{11}$ carboxylic acid esters optionally containing olefinic, acetylenic, or aryl moieties;
  (e) mixtures thereof; and
(ii) a carrier material.

Also in accordance with the present invention, there is provided a repellent composition for ants which is comprised of: (i) a derivative which is an ester that is a reaction product of an alcohol and a carboxylic acid, wherein at least the alcohol or the carboxylic acid is a repellent which meets one of the above formulae; and (ii) a carrier material.

Still in accordance with the present invention is a repellent composition for ants which is comprised of a (i) polymer composition having pendent functional groups, capable of reaction with the repellent, selected from the group consisting of carboxylic acid groups,—OH groups and mixtures thereof; and (ii) the repellents covalently bonded to the reactive groups.

Also in accordance with the present invention is a method for repelling ants from an area or object, which method comprises treating said area or object with an effective amount of a repellent composition selected from the above mentioned carboxylic acids, alcohols, ketones, and esters.

In a preferred embodiment of the present invention, there is provided an effective amount of the above compositions and a controlled release matrix.

5,587,401

DETAILED DESCRIPTION OF THE INVENTION

Figure 1:
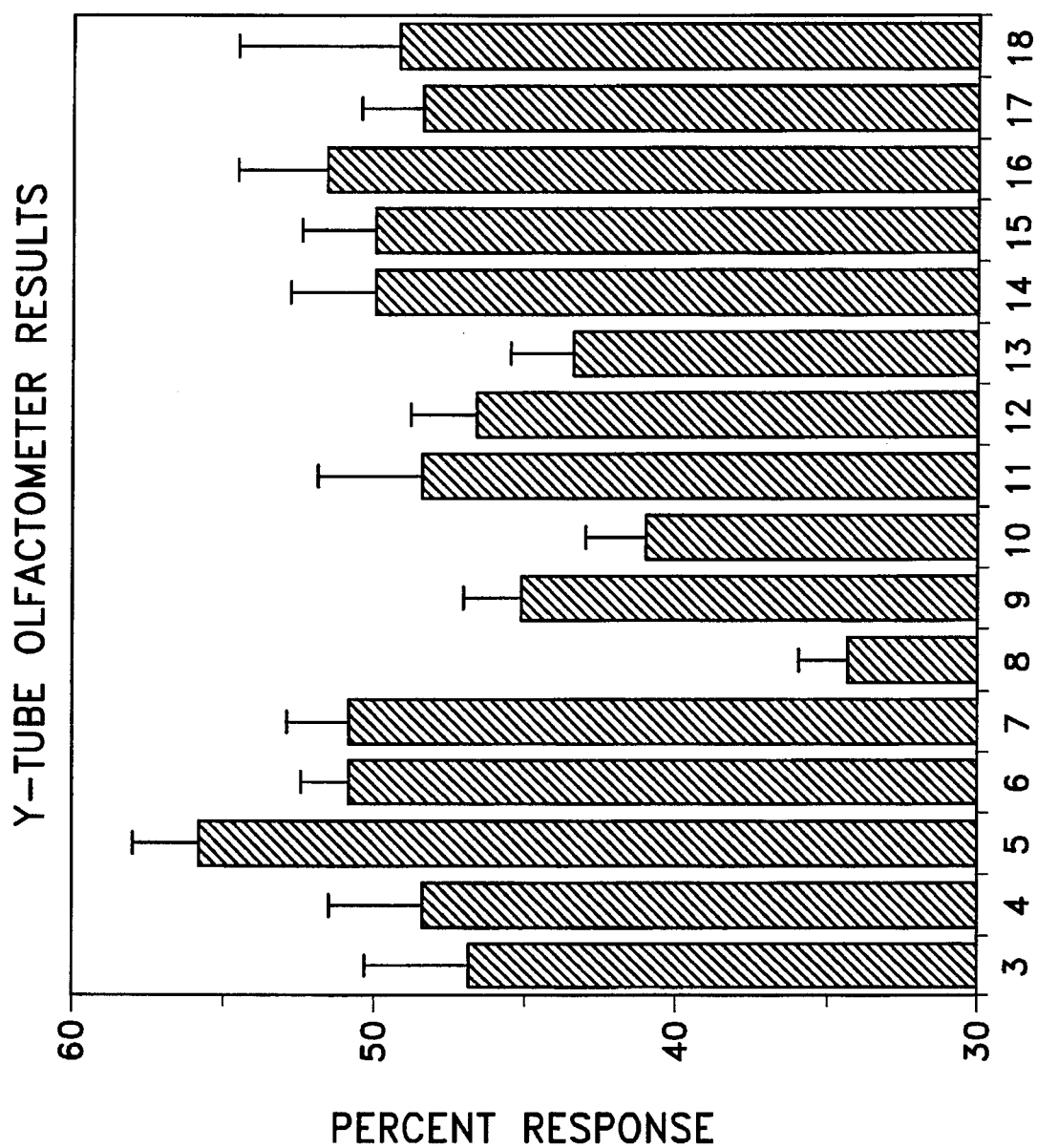
FIG. 1 is a bar graph of the percent response of ants placed in a Y-tube olfactometer wherein one of the chambers has the test sample at a concentration of 0.1% weight to volume. $C_3$ to $C_{18}$ straight chain carboxylic acids were tested. A response of 35% or less is considered repellent.

Preferred carboxylic acids suitable for use in the present invention include octanoic acid, 2-methyl-hexanoic acid, and trans-2-hexenoic acid. More preferred is octanoic acid.

Non-limiting examples of alcohols which are suitable for use in the present invention include those selected from the group consisting of 1-Octyn-3-ol, 1-Octen-3-ol, 4-Octanol, 2-Octen-4-ol, 3-Octen- 2-ol, 3-Octen-1-ol, 1-Hepten-3-ol, 1-Heptyn-3-ol, 2-Octanol, linalool, 1-Nonen-3-ol, 3-Octanol, 2-Octen-1-ol, tetrahydrolinalool, (Z)-5-Octen-1-ol, and 1-Octanol.

A non-limiting example of ketones which are suitable for use in the present invention are 1-Octyn-3-one, 1-Octen-3-one, 4-Octanone, 2-Octen-4-one, 3-Octen-2-one, 1-Hepten-3-one, 1-Heptyn-3-one, 2-Octanone, 1-Nonen-3-one, 3-Octanone, 2-Octen-1-one, 2-Heptanone,2-Nonanone, 2-Dodecanone.

Non-limiting examples of carboxylic acid esters which are suitable for use in the present invention include those selected from the group consisting of 1-Nonen-3-yl acetate and Ethyl-2-hydroxy-3-phenyl-3-butenoate.

Derivatives of the carboxylic acid and alcohol repellents of the present invention may also be used. An example of a type of derivative which is particularly suitable are esters which are the reaction product of an alcohol and a carboxylic acid, one or both of which are repellents of the present invention. It is preferred that both the alcohol and the carboxylic acid portion of the ester be repellents of the present invention. The ester

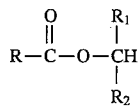

is the reaction product of R—COOH and

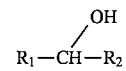

wherein R is a $C_5$ to $C_7$ branched or straight chain alkyl group; $R_1$ is H or a $C_1$ to $C_6$ alkyl group, optionally containing olefinic, acetylenic, or aryl moieties, and $R_2$ is a $C_2$ to $C_{13}$ alkyl group, optionally containing olefinic, acetylenic, or aryl moieties, wherein the carboxylic acid is a $C_6$ to $C_8$ carboxylic acid and the alcohol is a $C_6$ to $C_{14}$ alcohol. Upon hydrolysis, the ester will decompose and give up both the alcohol and carboxylic acid repellent. An advantage to using an ester is that the ester will most likely be less volatile because of its higher molecular weight. Furthermore, hydrolysis of the ester would provide a slow release of the repellent compounds.

Another type of derivative, called a pendent repellent, which is suitable for use herein, are polymers which contain an effective amount of pendent reactive groups capable of reaction with the repellents selected from carboxylic acid groups and—OH groups or mixtures thereof to which the repellents are attached. Non-limiting examples of polymers suitable for use herein include polyamides, polyesters, polyurethanes, and polyalkenes. The polymer having the acid and/or -OH groups will be used in combination with a repellent of the present invention so that the repellent will react with one or more of the acid or—OH groups of the polymer, thereby forming esters which are pendent on the polymer backbone (McCormick et al, *Controlled Release Pesticides*, ACS Symposium Series, Vol. 53, pp. 112–125, 1977; Harris et al, *Controlled Release Pesticides*, ACS Symposium Series, Vol. 53, pp. 102–111, 1977; Cardarelli, *Controlled Release Polymeric Applications*, ACS Symposium Series, Vol. 33, pp. 208–214, 1976; Meyers et al, Proc. Int. Symp. *Controlled Release Restic. Pharm.*, Plenum, N.Y., pp. 171–190, 1981. All Incorporated herein by Reference). Upon subsequent hydrolysis, a repellent carboxylic acid, alcohol, or both, will be released. The rate of hydrolysis can be controlled by adjusting the length of the pendent acid or—OH moiety in the polymer. Hydrolysis can occur under both basic and acidic conditions; e.g., in the soil. This type of derivative will yield a solid formulation which is readily distributed where needed. The pendent repellent can be mixed with soil and used with nursery stock.

It is preferred for commercial applications that the repellents of the present invention be applied with a carrier component. The carrier component can be a liquid or a solid material. Liquids suitable as carriers for the repellents of the present invention include both water and organic solvents. Non-limiting examples of organic solvents suitable for use in the present invention include acetone, hexane, lacquer, methanol, and methylene chloride. While most of the reagents of the present invention are not particularly soluble in water, they will form a suspension, or emulsion, in water which will be relatively stable and which will be suitable for applying to an area or object to be treated. It is more preferred that the repellent be soluble in the liquid carrier. The amount of repellent used will be at least an effective amount. The term "effective amount", as used herein, means that minimum amount of repellent needed to repel, or substantially prevent the ants from invading a treated area or object, when compared to the same area or object which is untreated. Of course, the precise amount needed will vary in accordance with the particular repellent composition used; the type of area or object to be treated; the number of days of repellency needed; and the environment in which the area or object is located. For example, if the object or area to be treated is situated outdoors and is exposed to the weather, then higher concentrations of repellent would be needed to be effective for a given period of time than if the object were indoors or under cover. The precise amount of repellent needed can easily be determined by one having ordinary skill in the art given the teaching of this application. The examples herein show typical concentrations which will be needed to repel ants, particularly fire ants.

Non-limiting examples of solid carrier materials which can be used in the practice of the present invention include diatomaceous earth, alumina, silica, clays, other suitable inorganic oxides, as well as powdered carbohydrates, such as corn starch, dextrans, and cellulose. The carrier may also be a solid substance, preferably one which will slowly release the repellent composition over a period of time. Non-limiting examples of slow release materials which are suitable for use herein include latex particles, capillary tubes, and microencapsulation. Of course, the type of area or object to be treated, and the degree of infestation in the vicinity of the area, or object to be treated, will dictate the type of carrier to be used. For example, when the object to be treated is a pot containing soil for nursery stock, it is preferred to use an aqueous suspension of the repellent.

The repellent compositions of the present invention can be combined with the solid carrier material by any appropriate means. For example, they may be combined by first dissolving or suspending, the repellent in a suitable solvent or other liquid; soaking the solid carrier material with the resulting solution or suspension, thereby either impregnating the repellent into, or depositing it onto, said solid carrier material; and, drying said treated carrier material to drive-off the solvent, or other liquid. The resulting repellent material can then be applied in powder form, for example, by spraying the area or object to be treated.

Having thus described the invention and its preferred embodiments, the following examples are presented to illustrate various embodiments of the present invention and should not be considered as limiting in any way.

EXAMPLE 1

0.1% wt.:vol. hexane solutions were prepared for each of a homologous series of $C_3$ to $C_{18}$ straight chain carboxylic acids. Each solution was placed in a Y-tube olfactometer. The olfactometer used herein is the one described in Isolation of the Trail Recruitment Pheromone of *Solenopsis invicta*, by R. K. Vander Meer, F. Alvarez, and C. S. Lofgren, Journal of Chemical Ecology, Vol. 14, No. 3, pp. 825–838, 1988, and which is incorporated herein by reference.

The Y-tube olfactometer is comprised of two 24/40 ground glass joints wherein each ring is sealed to one of the arms of a 5 cm Y-tube such that 1 cm of each Y-tube arm extends through the male half of one of the ground glass joints. A 5 cm piece of 0.6 cm ID tubing is ring sealed 1 cm into the female half of the ground glass joints. A baffle is provided at the center of the Y tube for controlling air streams and to prevent premature mixing of the sample. It also gives the ants a clearer choice. The baffle also narrows the openings to the choice chambers to the minimum size required for passage of a major ant worker. A test sample (10 l/worker equivalent) and a solvent blank (101) were each applied to a separate filter paper strip (0.3×2.5 cm, Whatman No. 1). Each was air dried and one was placed in one of the choice chambers and the other in the other chamber. Compressed air (breathing air quality) was split into two streams and passed into the two chambers. Each stream was regulated to 0.2 liters/min. for a total effluent flow rate of 0.4 liters/min. Approximately 50 to 70 ants from laboratory colonies were confined in a 2.5 cm piece of 0.9 cm ID Tygon tubing which was sealed at one end with wire gauze. The open end of the tubing was attached to the entrance stem leading to both chambers.

The initial choice of the first 20 ants that walked down the entrance tube and into one of the arms (chambers) of the Y tube was recorded. Ants that were not trapped in a chamber and came back to the entrance stem were not counted if they made another choice. After each test, the olfactometer was rinsed with acetone and dried. Each test sample was retested with worker ants from the same colony, but the choice chamber in which the sample and control were placed was reversed. This procedure eliminated any bias inherent in the olfactometer. A complete replicate was the sum of the results from the two tests. Data were analyzed statistically by a chi-squared test. The results are shown in Table I below and FIG. 1.

TABLE I

| Acid Chain Length | % Response |
|---|---|
| 3 | 46.8 ± 3.6 |
| 4 | 48.3 ± 3.3 |
| 5 | 55.8 ± 2.2 |
| 6 | 50.8 ± 1.7 |
| 7 | 50.8 ± 2.2 |
| 8 | 34.2 ± 1.7 |
| 9 | 45.0 ± 2.0 |
| 10 | 40.8 ± 2.2 |
| 11 | 48.3 ± 2.2 |
| 12 | 46.6 ± 2.2 |
| 13 | 43.3 ± 2.2 |
| 14 | 50.0 ± 2.9 |
| 15 | 50.0 ± 2.5 |
| 16 | 51.6 ± 3.0 |
| 17 | 48.3 ± 2.2 |
| 18 | 49.2 ± 5.5 |

Solutions which received greater than a 65% response are considered attractants. Those which received a 35% or less response are considered repellents, and those between 35% and 65% are considered neutral. The above Table evidences that only the $C_8$ straight chain carboxylic acid, octanoic acid, was effective for repelling ants at a 0.1% weight:volume concentration.

Example 2

1.0% weight:volume hexane solutions of 2-methylhexanoic acid and trans-2-hexanoic acid were prepared and the procedure of Example 1 above was repeated. The results are shown in Table II below.

TABLE II

| Carboxylic Acid | % Response |
|---|---|
| 2-methylhexanoic acid | 8.1 ± 3.2 |
| trans-2-hexanoic acid | 10.0 ± 2.5 |

EXAMPLE 3

A series of experiments were performed to test the effect of octanoic acid for preventing predation on parasites in capsules used in biological control programs. Trichogramma, a parasitic wasp bio-control agent, used against cotton pests, is released as pupae in small capsules from which the adults emerge within three days. In fire ant infested areas, the capsules are quickly found by foraging fire ants, penetrated, and the parasites eaten. Thus, such a bio-control agent is made ineffective. These experiments were designed to test whether or not the addition of octanoic acid to the capsules would prevent the ants from entering the capsules long enough to allow adult parasites to emerge.

The inner surfaces of five Trichogramma release capsules were treated with 200 uL of a 5% wt.:vol. solution of octanoic acid in acetone. The outer surfaces of another five capsules were treated with 200 uL of the same solution, and an additional five capsules were untreated. Five fly pupae were added to each of the 15 capsules, and the capsules were sealed with paraffin wax. Five fire ant colonies no larger then one (1) cell size were selected as test colonies. Each colony received a capsule treated on the inside, a capsule treated on the outside, and an untreated capsule. The capsules were placed approximately 10 cm from the perimeter of the colony cell. The response of the worker ants was monitored at 10 min and every hour thereafter for 5 hours. The capsules were then monitored daily at the following times from the beginning of the experiment: 1, 2, 3, 4, 7, 9, 11, and 16 days. On the fourth day, the colonies were fed for the first time since the start of the experiment.

Figure 2:
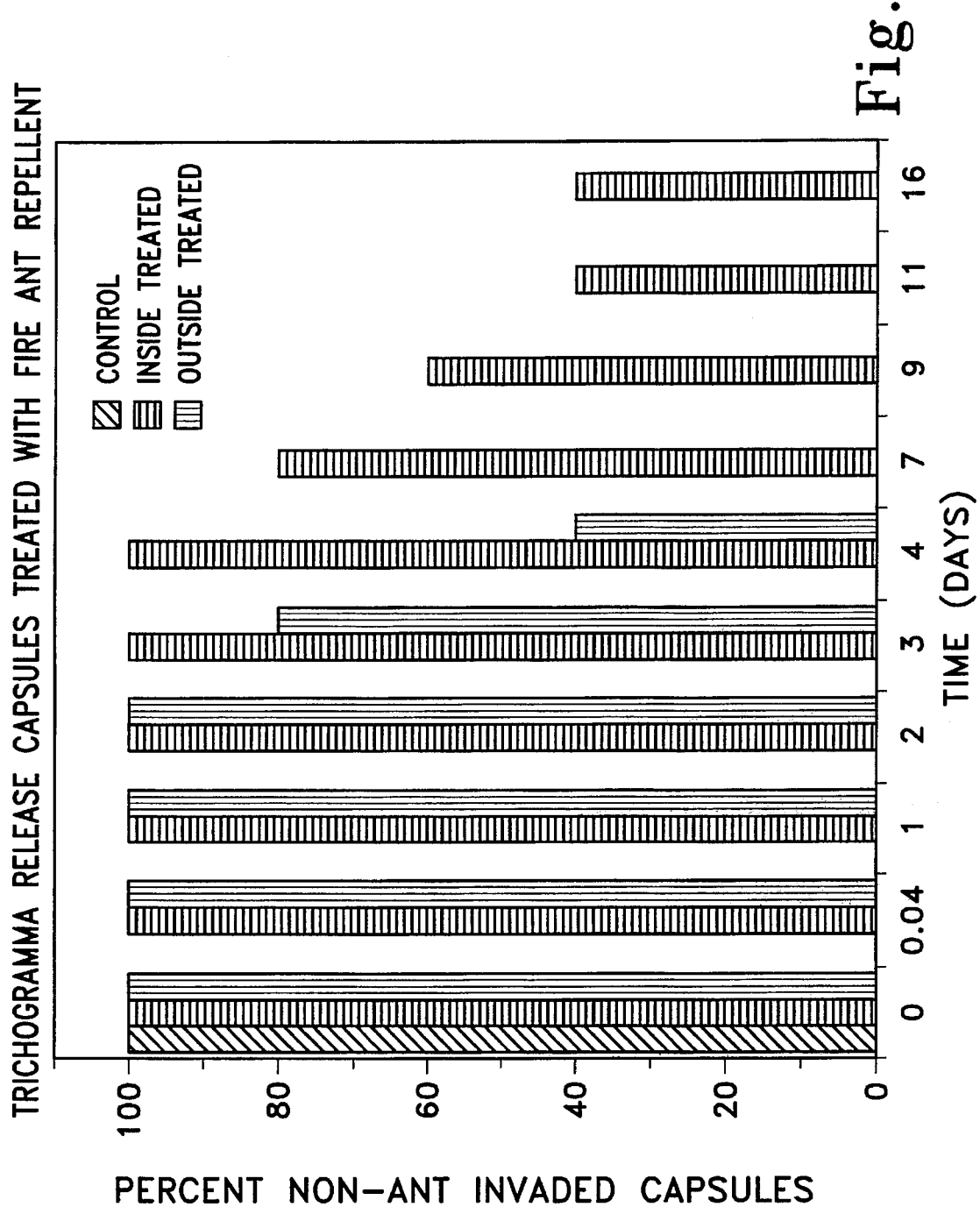
FIG. 2 is a bar graph of laboratory tests of the repellent effects of octanoic acid against fire ant invasion of Trichogramma release capsules.

It was observed that worker ants entered all control (untreated) capsules within one hour (3 by 5 min. and 2 by 1 hour). One capsule treated on the outside was invaded after 4 days, and by 9 days all five replicates had worker ants in them. The first invasion of a capsule treated on the inside Occurred at seven days posttreatment. By 16 days two capsules had not been invaded. The experiment was terminated after 16 days. See FIG. 2.

EXAMPLE 4

Figure 3:
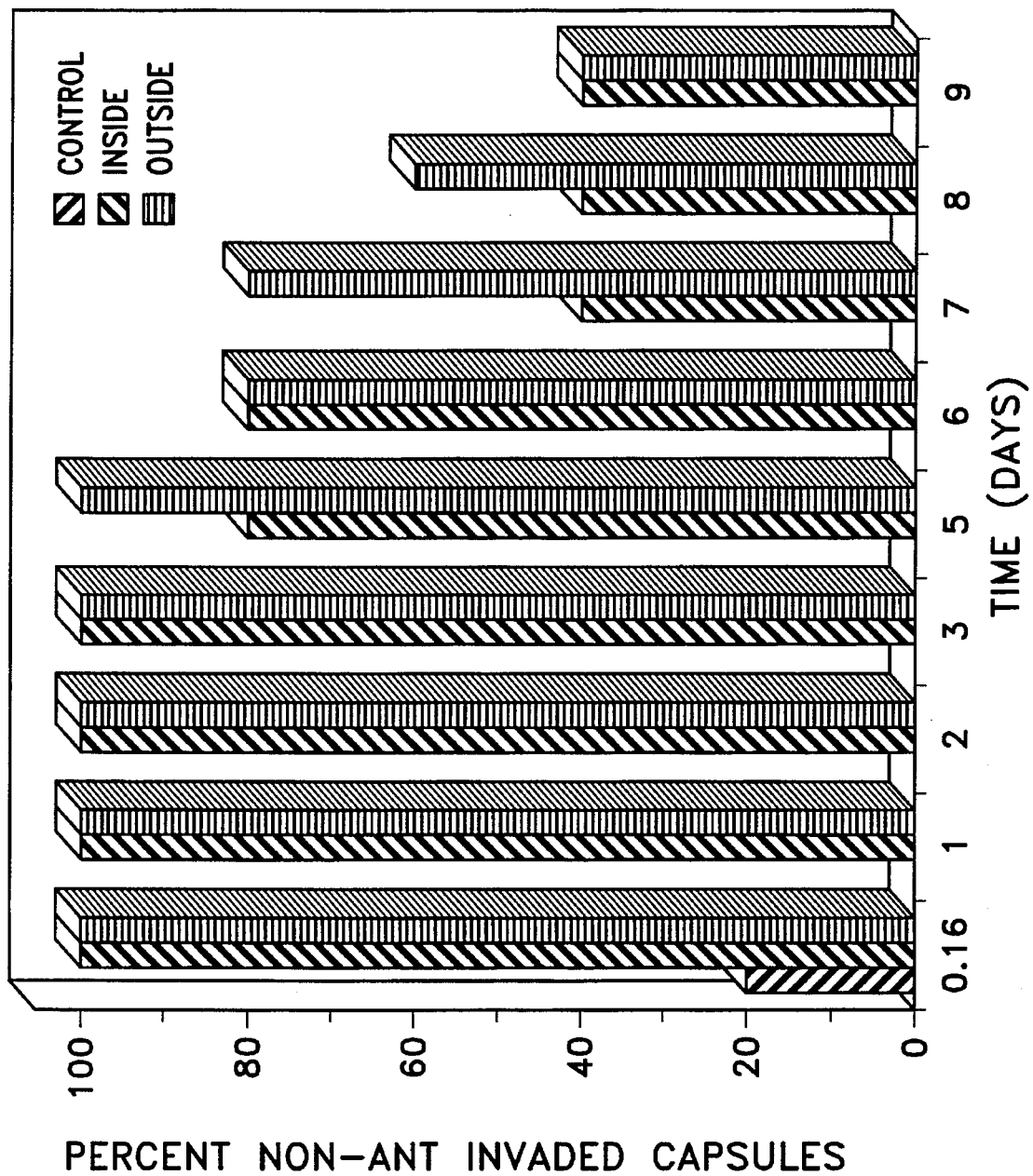
FIG. 3 is a bar graph of field tests of the repellent effects of octanoic acid against fire ants when the acid is impregnated on Trichogramma release capsules (treated on either the outside or inside).

The above experiment was repeated except that live flies were placed inside of the capsules to give the ants incentive to invade the capsules. The capsules were tested in a field infested with fire ants. Part of the field was marked into an eight by eight meter grid, providing 64 possible capsule locations. The 15 capsules were randomly placed in the grid locations. It was found that all of the five control capsules were invaded by ants within the first hour of testing. At the end of 5 days none of the capsules which were treated on the outside were invaded, and only 1 of the capsules which was treated on the inside was invaded. By the end of 9 days only three of the inside treated and three of the outside treated capsules were invaded. The experiment was stopped after 9 days. Thus, it can be clearly seen that octanoic acid is effective in protecting the capsules from fire ant invasion for a long enough period of time to allow Trichogramma parasitic wasps to emerge from the release capsules. See FIG. 3.

EXAMPLE 5

A series of experiments was performed to test the effect of a repellent of the present invention, octanoic acid, for preventing invasion of fire ants in nursery plants.

Figure 4:
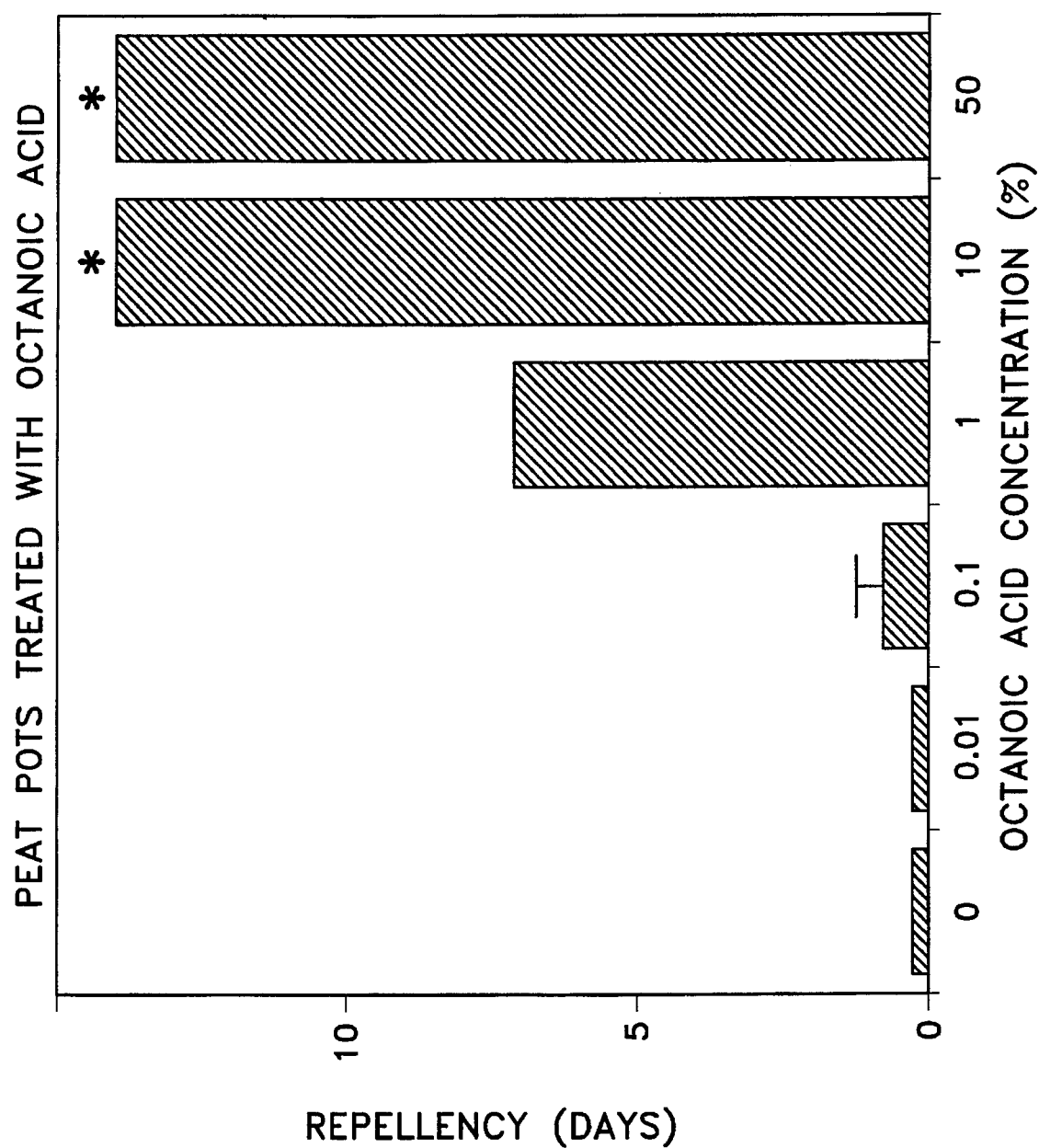
FIG. 4 is a bar graph of the efficacy of various concentrations of octanoic acid to prevent fire ant workers from moving into treated pots.
Experiment terminated.

Peat pots (75 mL) were treated with various concentrations of octanoic acid solutions in acetone, as set forth in Table III below. The concentrations ranged from about 0.01% to 50% wt.:vol. A control was also used which contained no octanoic acid. The samples were made by adding the appropriate volume of acetone to a known weight of octanoic acid, rather than by serial dilution. An application of 20 mL per pot resulted in complete wetting of the peat pot. The pots were allowed to dry in a fume hood for one hour, filled with moist nursery potting media, and then placed in metal trays (19×30×5 cm) containing small queen-right fire ant colonies (ca. 1,000 workers and five mL of immatures and a queen). There were three replicates for the control and each of the treatments. The pots were examined for ant invasion at 4 hr, 24 hr, and at the end of two weeks. The results are set forth in Table III below and FIG. 4.

TABLE III

| % Weight: Volume Octanoic acid | Days to Invasion |
| --- | --- |
| 0.01 | <0.16 ± 0.0 |
| 0.1 | <0.72 ± 0.48 |
| 1.0 | <5.0 ± 3.5 |
| 10.0 | >9.7 ± 7.5 |
| 50.0 | >14.0 ± 0.0 |
| Control | <0.16 ± 0.0 |

The above table shows that the two untreated pots were invaded within four hours. It also shows that increasing concentrations of octanoic acid gave increasing longevity of repellent activity. At the highest concentration, no ants had invaded the pots at the end of two weeks.

EXAMPLE 6

Figure 5:
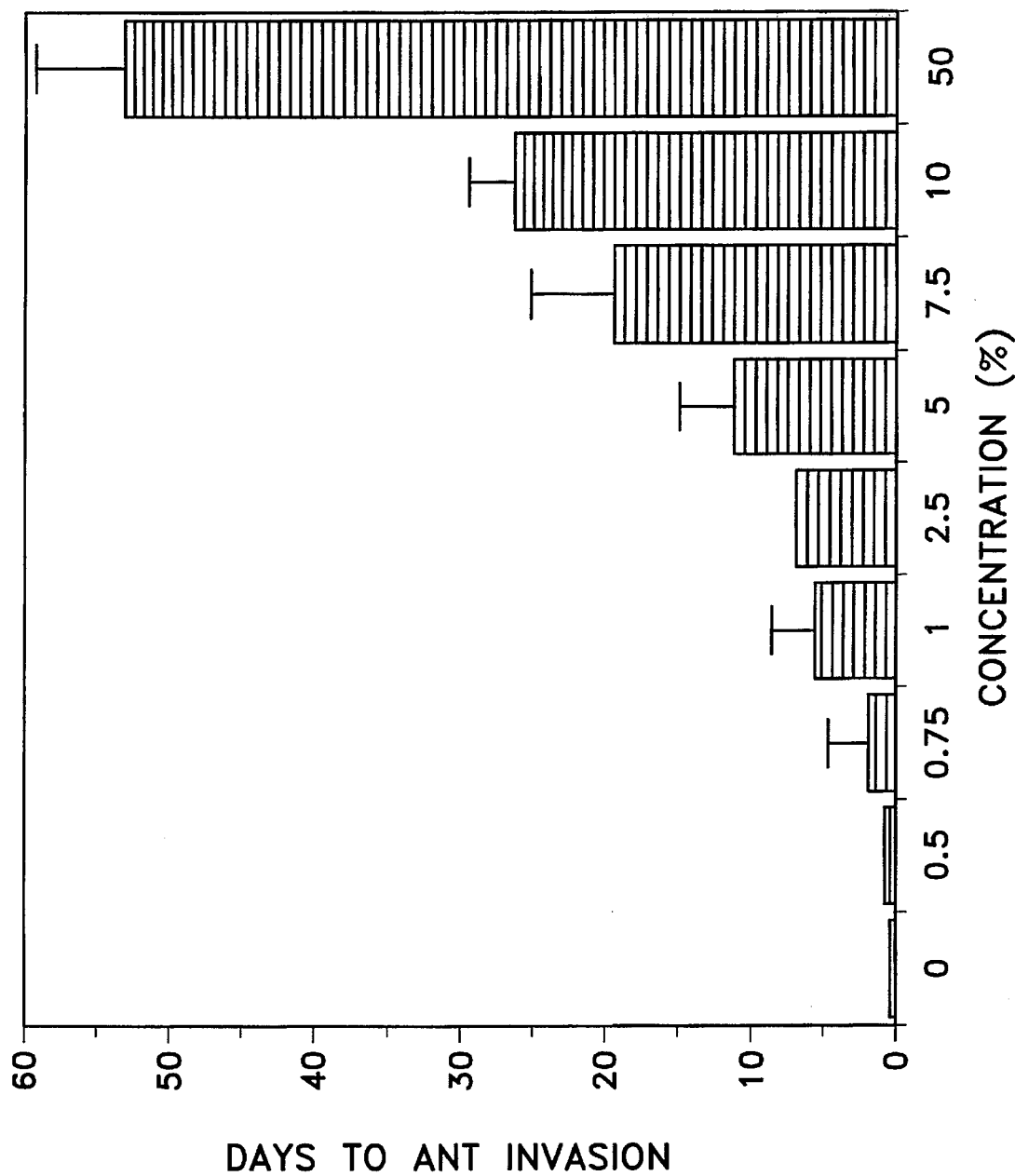
FIG. 5 is a bar graph of the efficacy of various concentrations of octanoic acid to prevent fire ant workers from moving into treated pots for up to 60 days.

Additional concentrations of octanoic acid in acetone were prepared and the procedure of Example 4 above was repeated except that there were five replicates of each treatment and a control. The experiment was monitored after 4 hr, 24 hr, then on a weekly basis for a total of eight weeks, at which time the experiment was terminated. The results are set forth in Table IV below and FIG. 5.

TABLE IV

| % Weight: Volume Octanoic acid | Days to Invasion |
| --- | --- |
| 0.5 | <7.0 ± 0.0 |
| 0.75 | <7.5 ± 4.9 |
| 1.0 | <12.25 ± 3.5 |
| 2.5 | <14.0 ± 0.0 |
| 5.0 | <18.2 ± 3.8 |
| 7.5 | <28.0 ± 8.6 |
| 10.0 | <39.2 ± 6.3 |
| 50.0 | >56.0 ± 0.0 |
| Control | <0.16 ± 0.062 |

The above table shows that octanoic acid repelled ants for increasing lengths of time with increasing concentrations. For example, the 10% solution had a mean repellent life of between 26 days and 38 days. Only one of the five 50% treatments was invaded by ants after 56 days, when the experiment ended.

EXAMPLE 7

Figure 6:
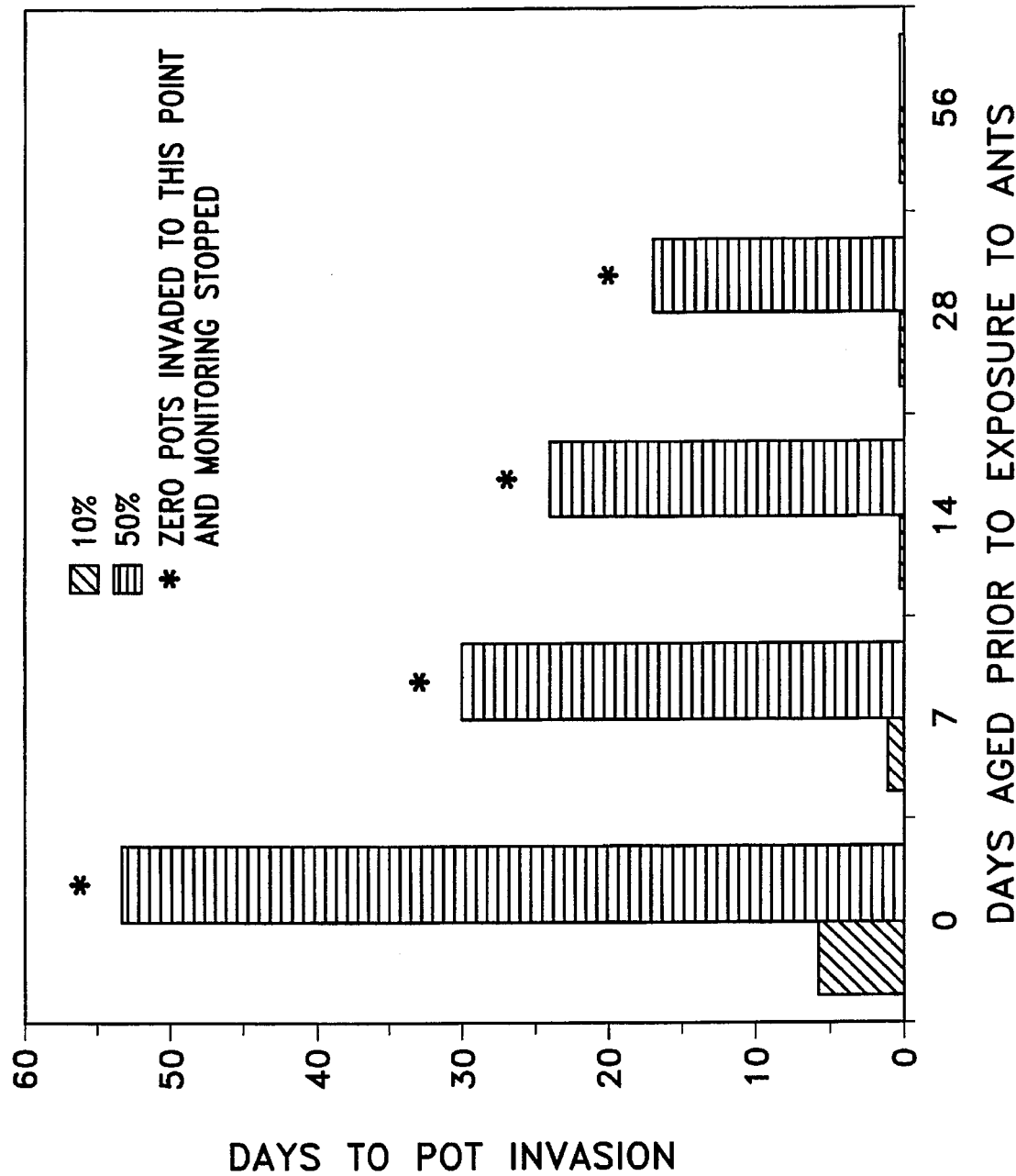
FIG. 6 is a bar graph of the effects of aging treated peat pots prior to exposure to fire ant colonies.

A series of experiments were carried out to test the effectiveness of octanoic acid for repelling fire ants from peat pots when subjected to the outdoor elements. Concentrations of 10% wt.:vol. and 50% wt.:vol. octanoic acid in acetone solutions were prepared and applied to peat pots as described in the previous examples. The treated pots were filled with moist soil and exposed to the elements outdoors. After each of 0, 7, 14, 28, and 56 days, three pots were taken to the laboratory and evaluated for repellent activity against laboratory fire ant colonies. It was observed that all treatments of 50% octanoic acid kept 100% of the ants away through 28 days of aging. Between 28 days and 56 days, there were heavy rains (>5 inches), which may explain the lack of any repellency at 56 days of aging. See FIG. 6.

EXAMPLE 8

Figure 7:
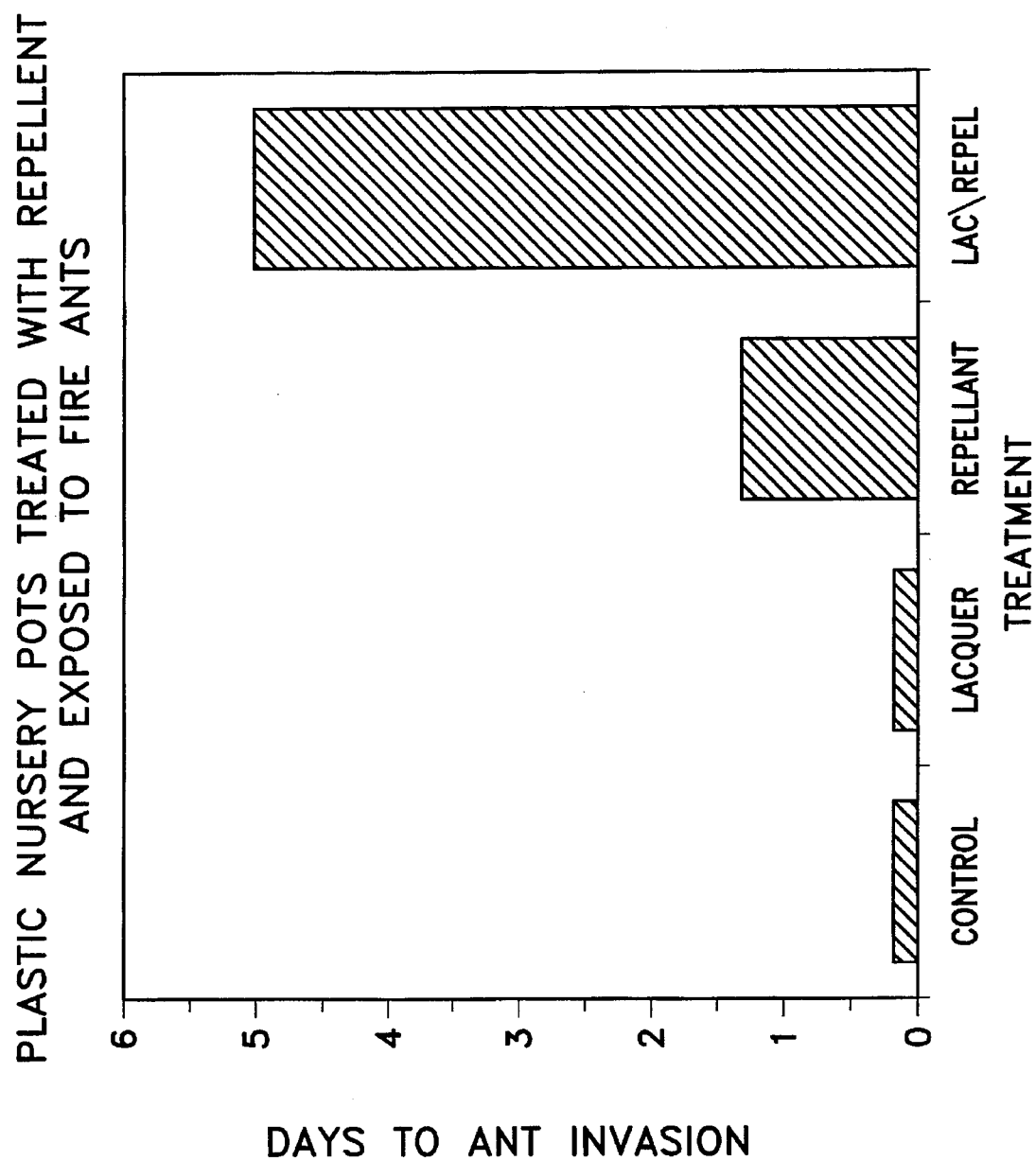
FIG. 7 is a bar graph of the repellent effects of octanoic acid in acetone or lacquer painted onto the lower half and bottom of plastic pots.

Instead of peat pots, which readily absorb the octanoic acid solutions, plastic nursery pots were used. Two octanoic acid treatments were evaluated: a) octanoic acid in acetone, and b) octanoic acid in lacquer. The two controls were acetone, and acetone plus lacquer. All except the acetone control were formulated as 1 to 1 solutions. The lower half and bottom of the pots were painted with the solutions. The pots were observed for fire ant invasion and the results are set forth in Table V below and FIG. 7.

TABLE V

| Treatment | Days to Invasion |
| --- | --- |
| Octanoin acid | 1.33 ± 0.33 |
| Lacquer | 0.17 ± 0.0 |
| Octanoic Acid + Lacquer | 5.0 ± 1.53 |
| Control | 0.17 ± 0.0 |

The above table shows that octanoic acid by itself had significant repellent activity, but more interesting are the results from the combination of lacquer and octanoic acid. It appears as if the lacquer slows the loss of octanoic acid, thus extending its effectiveness. These results evidence to the potential of the repellent in controlled release formulations.

EXAMPLE 9

A four choice soil bioassay was devised that allowed the determination of whether or not newly mated queen fire ants would discriminate between soils in which to build their nuptial chamber (found a colony). Two control choices (soil plus water) and two treatment choices were used. The treatments were: (i) soil plus octanoic acid at 0.26% (W/W) and (ii) soil plus octanoic acid at 1.3% (W/W). Three newly mated queen fire ants were placed in the middle of each of the four choice quadrants. They could move freely from one quadrant to the other. There were four replicates. After three days the soil from each quadrant was removed and searched for queens.

Figure 8:
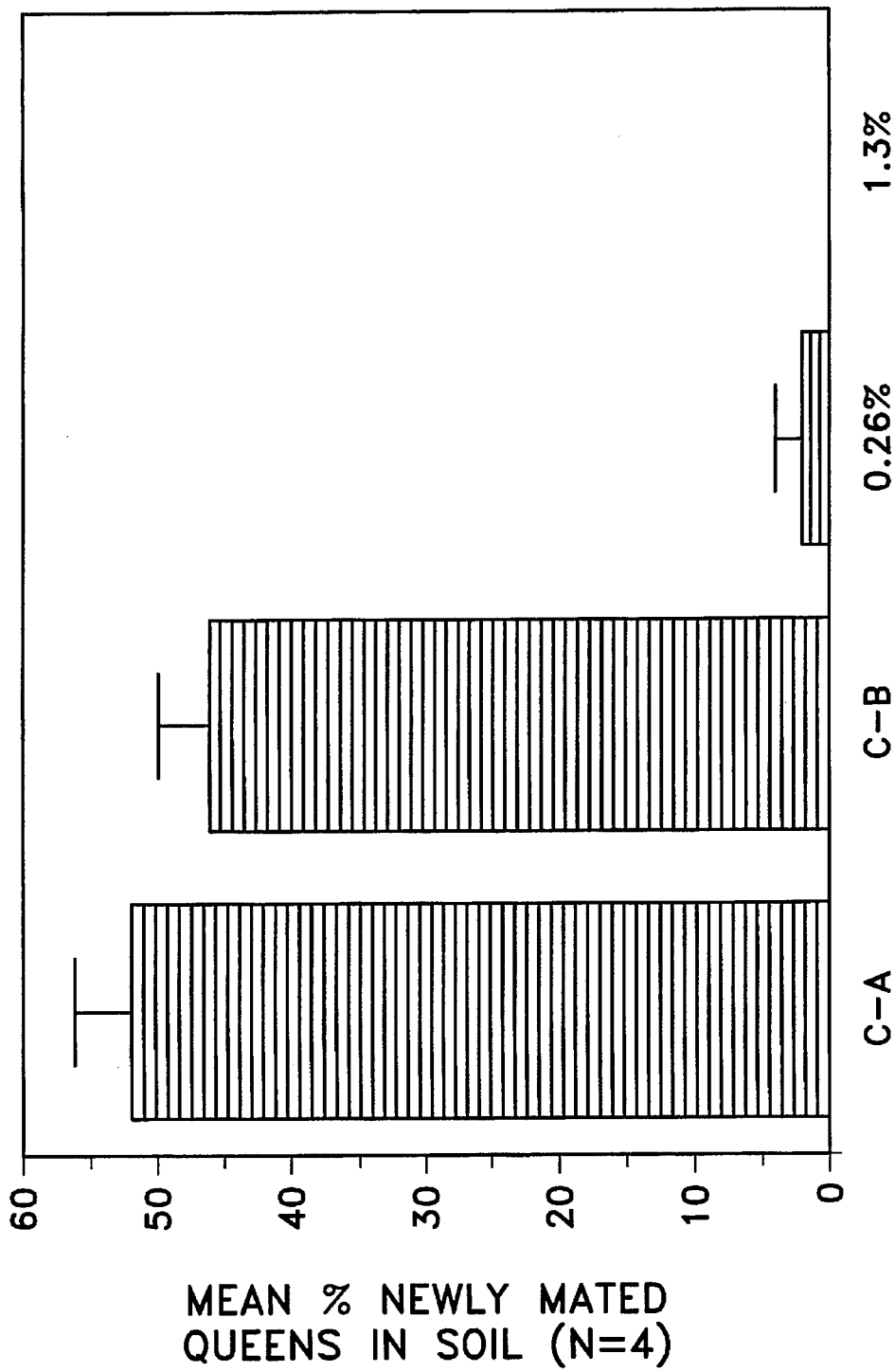
FIG. 8 is a bar graph of the effect of octanoic acid/soil on a newly mated queen's choice of where to found her colonies. C–A and C–B are controls

It was observed that only one of the 48 queens released into the four replicates chose one of the octanoic acid treated quadrants. All others picked the control soil. These results indicate that it is possible to exclude newly mated queens from an area using octanoic acid as a repellent. See FIG. 8.

EXAMPLE 10

The procedure of Example 1 above was followed for different chemicals at either a 1% weight:volume or 0.1% weight:volume concentration. The results are shown in Table VI below.

TABLE VI

| Number | Chemical Name | Conc. (% weight: volume) | Response % |
| --- | --- | --- | --- |
| Not assigned | 1-heptanol | 1.0 | 15 ± 6.6 |
| Not assigned | 2-heptanol | 1.0 | 20 ± 4.3 |
| Not assigned | S(+) 2-octanol | 1.0 | 5 ± 2.5 |
| Not assigned | 1-nonanol | 1.0 | 5 ± 2.5 |
| Not assigned | 2-nonanol | 1.0 | 1.7 ± 1.4 |
| Not assigned | 1-decanol | 1.0 | 3.3 ± 3.8 |
| Not assigned | 1-dodecanol | 1.0 | 38.3 ± 17.7 |
| Not assigned | 2-dodecanol | 1.0 | 25 ± 7.5 |
| Not assigned | 1-tetradecanol | 1.0 | 33.3 ± 2.8 |
| Not assigned | 2-tetradecanol | 1.0 | 45.8 ± 7.2 |
| 82521-a | 1-Octyn-3-ol | 1.0 | 10 ± 5.0 |
| Not assigned | 1-Octen-3-ol | 1.0 | 10 ± 2.5 |
| 37214 | 4-Octanol | 1.0 | 14.2 ± 5.2 |
| 28628 | 2-Octen-4-ol | 1.0 | 15.8 ± 5.77 |
| 39568-a | 3-Octen-2-ol | 1.0 | 16.6 ± 2.88 |
| 39566-a | 3-Octen-1-ol | 1.0 | 16.6 ± 5.20 |
| 28621 | 1-Hepten-3-ol | 1.0 | 17.5 ± 2.5 |

TABLE VI-continued

| Number | Chemical Name | Conc. (% weight: volume) | Response % |
| --- | --- | --- | --- |
| 37262 | 1-Heptyn-3-ol | 1.0 | 17.5 ± 5.0 |
| 5589 | 2-Octanol | 1.0 | 20 ± 3.81 |
| 36553 | 1-Nonen-3-yl acetate | 1.0 | 24.2 ± 3.81 |
| 942 | Linalool | 1.0 | 25.8 ± 3.81 |
| 54065 | 3-Octen-2-one | 1.0 | 26.6 ± 3.81 |
| 8-60A | 1-Nonen-3-ol | 1.0 | 28.3 ± 6.29 |
| 37213 | 3-Octanol | 1.0 | 28.3 ± 12.5 |
| 36043-a | 2-Octen-1-ol | 1.0 | 29.3 ± 5.77 |
| 24903 | Tetrahydrolinalool | 1.0 | 29.2 ± 3.81 |
| TPM 10-109 | Ethyl 2-hydroxy-3-phenyl-3-butenoate | 1.0 | 30 ± 2.50 |
| 39567 | (Z)-5-Octen-1-ol | 1.0 | 31.6 ± 1.44 |
| 2169 | 1-Octanol | 1.0 | 33.3 ± 1.44 |
| TPM 10-152 | 2-Ethoxyethyl 2-hydroxy 3-phenyl-3-butenoate | 1.0 | 34.2 ± 8.3 |
| TPM 10-127 | Propyl 2-hydroxy-3-phenyl-3-butenoate | 1.0 | 39.2 ± 2.88 |
| 34394 | 1-Octen-3-yl acetate | 1.0 | 40 ± 9.01 |
| TPM 10-158-2 | 3-methylbutyl 2-hydroxy-3-phenyl-3-butenoate | 1.0 | 40.8 ± 3.81 |
| 10519 | Neroidol | 1.0 | 42.5 ± 4.99 |
| TPM 10-133 | Isopropyl 2-hydroxy-3-phenyl-3-butenoate | 1.0 | 42.5 ± 6.61 |
| TPM 10-150 | Allyl 2-hydroxy-3-phenyl-3-butenoate | 1.0 | 45.8 ± 7.63 |
| 28606 | 1-Penten-3-ol | 1.0 | 47.5 ± 4.33 |
| TPM 10-62-2 | Ethyl alpha-hydroxy-4-tert-butyl-1-cyclohexene-1-ylacetate | 1.0 | 47.5 ± 4.99 |
| 28424-b | 3-buten-2-ol | 1.0 | 48.3 ± 3.81 |
| 34096-x | Ethyl beta-chloro-alpha hydroxy-beta methylhydro-cinnamate | 1.0 | 51.6 ± 2.88 |
| 34090-x | Propyl beta-chloro-beta-ethyl-alpha hydroxyhydro-cinnamate | 1.0 | 56.6 ± 2.88 |
| 34097-x | Propyl beta-chloro-alpha-hydroxy-beta methyl-hydrocinnamate | 1.0 | 59.1 ± 3.81 |
| TPM 10-63-2 | Ethyl alpha-hydroxy-alpha-methyl-4-tert butyl-1-cyclohexane-1-ylacetate | 1.0 | 60 ± 8.66 |
| Not assigned | 10-undecenic acid | 1.0 | 48.3 ± 3.8 |
| Not assigned | trans-traumatic acid | 1.0 | 56.9 ± 8.8 |
| 14312 | Allyl alcohol | 1.0 | 64.2 ± 5.77 |
| 28628 | 2-Octen-4-ol | 0.1 | 27.5 ± 6.61 |
| Not assigned | 1-Octen-1-ol | 0.1 | 31.6 ± 2.88 |
| 39566 | 3-Octen-1-ol | 0.1 | 32.5 ± 2.49 |
| 82521 | 1-Octyn-3-ol | 0.1 | 34.2 ± 5.2 |
| 37262 | 1-Heptyn-3-ol | 0.1 | 45 ± 7.5 |
| 5598 | 2-Octanol | 0.1 | 48.3 ± 3.81 |
| 28621 | 1-Hepten-3-ol | 0.1 | 50 ± 4.33 |
| 37214 | 4-Octanol | 0.1 | 51.6 ± 8.77 |

The reagents tested in this example which meet the requirements of the present invention for repelling ants are those having a % response equal to, or less than, 35%.

What is claimed is:

1. A method for repelling ants from an object or area comprising treating the object or area with an ant repelling composition comprising (i) an effective amount of 3-octen-2-one; and (ii) a carrier material.

* * * * *